(12) United States Patent
O'Lenick et al.

(10) Patent No.: US 7,868,208 B1
(45) Date of Patent: Jan. 11, 2011

(54) POLYQUATERNARY ALKYL POLYMERS

(75) Inventors: Kevin A. O'Lenick, Dacula, GA (US); Thomas G. O'Lenick, Dacula, GA (US); Anthony J. O'Lenick, Jr., Dacula, GA (US)

(73) Assignee: Surfatech Corporation, Dacula, GA (US)

( * ) Notice: Subject to any disclaimer, the term of this patent is extended or adjusted under 35 U.S.C. 154(b) by 644 days.

(21) Appl. No.: 11/903,693

(22) Filed: Sep. 25, 2007

Related U.S. Application Data

(63) Continuation-in-part of application No. 11/409,411, filed on Apr. 24, 2006, now abandoned.

(51) Int. Cl.
*C07C 211/63* (2006.01)
*C11D 1/62* (2006.01)

(52) U.S. Cl. .................................... 564/295; 424/70.28

(58) Field of Classification Search .................. 564/295; 424/70.28
See application file for complete search history.

(56) References Cited

U.S. PATENT DOCUMENTS

| | | | | |
|---|---|---|---|---|
| 5,066,414 A | * | 11/1991 | Chang | 510/524 |
| 6,503,876 B1 | * | 1/2003 | Broeckx | 510/349 |
| 6,982,078 B1 | | 1/2006 | O'Lenick | |

* cited by examiner

*Primary Examiner*—Shaojia Anna Jiang
*Assistant Examiner*—Jonathan S Lau

(57) ABSTRACT

The present invention relates to a novel class of polymeric compounds having specific highly crosslinked cationic or amphoteric structure. These products are produced without free radical monomers ands are based upon an alkyl diamine which has been reacted to produce a di-tertiary amine compound. The diamine has alkyl groups present the contribute hydrophobicity to the molecule and once crosslinked provide outstanding benefits vis-à-vis conditioning and softening to the hair and skin. The presence of the two amine groups and selection of the proper alkyl group allows for the synthesis of a high molecular weight cationic compound which is extremely substantitive to human skin and are well tolerated by human tissue making them suitable for use preparation of barrier products for personal care applications.

18 Claims, No Drawings

POLYQUATERNARY ALKYL POLYMERS

RELATED APPLICATION

This application is a continuation in part of application Ser. No. 11/409,411 now abandoned filed Apr. 24, 2006

FIELD OF THE INVENTION

The present invention relates to a novel class of polymeric compounds having specific highly crosslinked cationic or amphoteric structure. These products are produced without free radical monomers ands are based upon an alkyl diamine which has been reacted to produce a di-tertiary amine compound. The diamine has alkyl groups present the contribute hydrophobicity to the molecule and once crosslinked provide outstanding benefits vis-à-vis conditioning and softening to the hair and skin. The presence of the two amine groups and selection of the proper alkyl group allows for the synthesis of a high molecular weight cationic compound which is extremely substantitive to human skin and are well tolerated by human tissue making them suitable for use preparation of barrier products for personal care applications.

BACKGROUND OF THE INVENTION

It is very desirable to provide a material from aqueous solution that will condition the hair and still be compatible with anionic surfactants. This allows for the preparation of clear two in one shampoo systems, clear 2 in one shower gels, and clear two in one bath products. By two in one products in meant, a product that contains both anionic surfactant, most commonly sulfates and ether sulfates and a cationic conditioning agent. The anionic surfactant is the detergent, which cleans the hair or skin, and the cationic product is for conditioning providing softness, slip and feels to the skin. The problem with such product has always been the incompatibility of the anionic and cationic surfactants with each other. When many of these products are present in the same solution an insoluble salt forms making a cosmetically unacceptable white gunk that does not stay in solution.

As will become clear, by making a very large molecule the present invention results in a we call a soft quaternary compound. By soft quaternary compound is meant one that not withstanding its cationic charge is of a structure so that when placed in water along with the anionic surfactant, a clear stable solution is obtained. Surprisingly, because of the high molecular weight of the quaternary compound, the deposition on the hair and skin is increased. While not wanting to be held to only one mechanism, we believe there rather than a precipitate observed with so-called hard quats, compounds of the present invention form a self-assembling complex between the anionic and cationic surfactant. This complex, while water-soluble is large enough to disrupt hydrogen bonding between water molecules, and as such energetically, the complex will be deposited on the skin or hair leaving the remaining solution at the lowers free energy level.

The self-assembling aspect of the present invention, which we believe is the result of orientation of the salt of the cationic compounds of the present invention and the anionic surfactants present in solution, can be demonstrated by the fact that upon initial mixing of the components, a hazy or cloudy dispersion occurs. With suitable mixing, this hazy dispersion becomes a solution and the viscosity increases.

The compounds of the present invention can be formulated into body washes and other skin products and hair care products to provide a "delivery system" for conditioning the hair or skin. The high molecular weight of the quat and the fact that the point charges are far apart in the molecule results in through and efficient deposition on the hair or skin. This provides uniformity of conditioning agent over the entire hair of skin surface. This is particularly important for applications on hair for people with long hair. In general the long hair is more damaged, dry and in need of conditioning at the tip area, than near the root. The hair closest to the scalp is newer, less damaged, and less in need of conditioning. This dichotomy of hair condition is more effectively treated by the complexes formed by the current invention than by other quats. In addition, the di-nature of the compounds provides for outstanding substantivity of the molecule allow for very mild natural like materials that can be used in products where low irritation is important.

U.S. Pat. No. 6,331,293 issued Dec. 18, 2001 to Smith et al describes phosphobetaines that are derived from dimer acid. Unlike the compounds of the present invention, these materials are amphoteric surfactants and are barriers when applied to the skin. It is stated that the compounds are "extremely substantitive to human skin and are well tolerated by human tissue making them suitable for use preparation of barrier products for personal care applications". Unlike these materials, the compounds of the present invention are not amphoterics, but are quats, are not barriers but are conditioning agents that do not build up on the hair or skin.

U.S. Pat. No. 6,982,078, issued Jan. 3, 2006, to O'Lenick, Jr., et al. entitled Dimer amidopropyl dimethyl poly-quaternary compounds a novel class of polymeric compounds having specific quaternized amine based upon a dimer acid amido amine quaternary compound. Dimer acid is a C-36 diacid having a cyclic structure and two amine groups that allow for the synthesis of a high molecular weight cationic compound which is extremely substantitive to human skin and are well tolerated by human tissue making them suitable for use preparation of barrier products for personal care applications. This patent is incorporated herein by reference. The product of the '078 patent while very interesting for soma applications, have limited ability to vary the hydrophobicity (the "alkyl group of the present invention), can only be a cyclic structure and are limited to methyl groups on the quaternary compounds, As will become clear, the present invention the ability to tailor the molecule by varying the alkyl group, the groups linked to the quaternized nitrogen result in a series of polymers heretofore unavailable.

Many of the polymers used today in the personal care application area are derived from free radical polymerization of vinyl containing groups. These include the polymerization of acrylic acid, acrylamide, cationic acrylic derivatives and a host of others. There has been a growing concern that free radical polymers may represent a safety issue if there is any free vinyl monomer. Over time steps have been taken to reduce free vinyl monomer in the polymers made using free radical chemistry. None the less, many cosmetic companies are choosing not to use free radical polymers at all. There are few choices for polymers that are not free radical and offer good conditioning to the hair and skin. The compounds of the present invention are such a class of material. They do not use free radical systems or free radical reactants. This is a major advantage to consumers.

The references cited do not offer the surprising and unexpected properties offered by the products of the current invention.

SUMMARY OF THE INVENTION

Objective of the Invention

It is the objective of the invention to provide a novel series of polymeric alkyl compounds and a process of its use which comprises contacting the skin with an effective conditioning concentration of the novel polymers when applied in aqueous solution containing anionic surfactants. These anionic surfactants are preferably fatty sulfates and fatty ether sulfates having between 1 and 4 moles of ethylene oxide present. The polymeric nature of these materials makes them very substantive and minimally penetrating to the skin, making them both non-toxic and non-irritating.

In accordance with the present invention, we have now been discovered a novel polymer which conforms to the following structure:

wherein:
A is

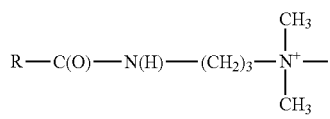

R is alkyl having between 7 and 27 carbon atoms and includes linear, branched, saturated unsaturated and polyunsaturated;
B is $CH_2$—$CH(OH)CH_2$.
C is:

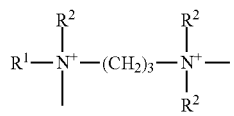

$R^1$ is selected from the group consisting of
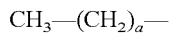
and
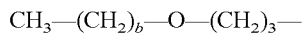
a is an integer ranging 7 and 27 carbon atoms and includes linear, branched, saturated unsaturated and polyunsaturated;
b is an integer ranging 7 and 27 carbon atoms and includes linear, branched, saturated unsaturated and polyunsaturated;
$R^2$ is selected from the group consisting of
and
M is selected from the group consisting of Na, K, and H;
x, y and z are independently integers ranging from 0 to 20, with the proviso that x+y+z be greater than 1;
n is an integer ranging from 1 to 2000.

It will clearly be understood that the nature of the "$R^2$" group determines not only solubility in water but ionic nature of the species.

When "$R^2$" is

The product is a poly-cationic having only a (+) charge on nitrogen.

Alternatively, when "$R^2$" is
—$(CH_2)_2C(O)O^-M^+$

The product is a poly amphoteric having a (+) charge on nitrogen and a (−) charge on the carboxyl group.

The present invention is also directed to a process for very efficiently conditioning the skin and hair from aqueous solution containing anionic surfactant. The complex that forms is very efficient in providing conditioning and can be used at concentrations as low as 0.5% by weight in a shampoo formulation. This is very important in products where low irritation is important like baby shampoo and bubble bath products.

The process for conditioning hair comprises contacting the hair with an effective conditioning concentration of a quaternary compound, which conforms to the following structure:

wherein:
A is

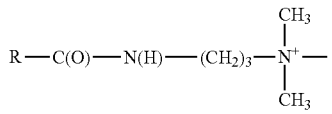

R is alkyl having between 7 and 27 carbon atoms and includes linear, branched, saturated unsaturated and polyunsaturated;
B is $CH_2$—$CH(OH)CH_2$—
C is

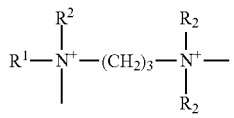

$R^1$ is selected from the group consisting of
and
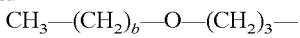
a is an integer ranging 7 and 27 carbon atoms and includes linear, branched, saturated unsaturated and polyunsaturated;
b is an integer ranging 7 and 27 carbon atoms and includes linear, branched, saturated unsaturated and polyunsaturated;
$R^2$ is selected from the group consisting of
—$(CH_2CH_2O)_x$—$(CH_2CH(CH_3O)y$-$(CH_2CH_2O)_z H$
and
—$(CH_2)_2C(O)O^-M^+$
M is selected from the group consisting of Na, K, and H;
x is an integer ranging from 1 to 2000.

The preferred effective conditioning concentration ranges from 0.5% to 25% by weight.

The polymers of the present invention are made in polar solvent, typically water, but can also be made in propylene glycol, polyoxyalkylene glycols and PEG/PPG dimethicone or combinations thereof. The selection of the proper solvent or combinations of solvents will determine the viscosity of the final polymer.

The use of PEG/PPG dimethicone as a solvent results not only in a relatively low viscosity product, but also results in a composition that has extremely efficient deposition on hair and skin, making the compositions highly desirable in personal care applications.

PREFERRED EMBODIMENTS

In a preferred embodiment $R^2$ is —$(CH_2CH_2O)_x$—$(CH_2CH(CH_3O)y$-$(CH_2CH_2O)_zH$.
In a preferred embodiment $R^2$ is —$(CH_2)_2(CH_2)_a$—.
In a preferred embodiment $R^1$ is $CH_3$—$(CH_2)_a$—.
In a preferred embodiment $R^1$ is $CH_3$—$(CH_2)_b$—O—$(CH_2)_3$—.
In a preferred embodiment R is $CH_3(CH_2)_6$—.
In a preferred embodiment, R is $CH_3(CH_2)_8$—.
In a preferred embodiment, R is $CH_3(CH_2)_{10}$—.
In a preferred embodiment R is $CH_3(CH_2)_{12}$—.
In a preferred embodiment, R is $CH_3(CH_2)_{14}$—.
In a preferred embodiment, R is $CH_3(CH_2)_{16}$—.
In a preferred embodiment R is $CH_3(CH_2)_{18}$—.
In a preferred embodiment, R is $CH_3(CH_2)_{20}$—.
In a preferred embodiment, R is $CH_3(CH_2)_{22}$—.
In a preferred embodiment R is $CH_3(CH_2)_{24}$—.
In a preferred embodiment, R is $CH_3(CH_2)_{26}$—.
In a preferred embodiment x is 1.

DETAILED DESCRIPTION OF THE INVENTION

The present invention is directed to novel polymers, which conform to one of the following structure:
A-(B-C)$_n$-B-A
wherein:
A is

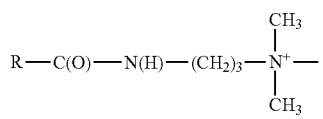

R is alkyl having between 7 and 27 carbon atoms and includes linear, branched, saturated unsaturated and polyunsaturated;
B is $CH_2$—$CH(OH)$ $CH_2$—
C is:

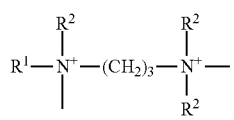

$R^1$ is selected from the group consisting of
  $CH_3$—$(CH_2)_a$—
and
  $CH_3$—$(CH_2)_b$—O—$(CH_2)_3$—
a is an integer ranging 7 and 27 carbon atoms and includes linear, branched, saturated unsaturated and polyunsaturated;
b is an integer ranging 7 and 27 carbon atoms and includes linear, branched, saturated unsaturated and polyunsaturated;
$R^2$ is selected from the group consisting of
  —$(CH_2CH_2O)_x$—$(CH_2CH(CH_3O)y$-$(CH_2CH_2O)_zH$
and
  —$(CH_2)_2C(O)O^-M^+$ M is selected from the group consisting of Na, K, and H;
x, y and z are independently integers ranging from 0 to 20, with the proviso that x+y+z be greater than 1;
n is an integer ranging from 1 to 2000.

The compounds of the present invention are made reaction is a series of steps. The first converts a commercially available diamine or ether diamine into a di tertiary amine.
This is done using one of two reactions;

1a. Reaction with Acrylic Acid (Alkyl Di-amines)

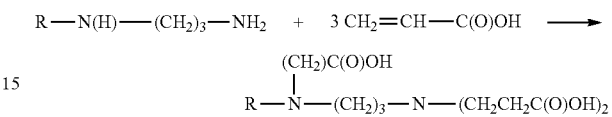

As will be clearly noted the result is two tertiary amines. This is a necessary step for carrying out the subsequent reactions.

1b. Reaction with Acrylic Acid (Alkyl Ether Di-amines)
The reaction is also carried out with an ether diamine.

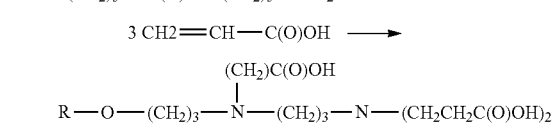

The ether diamine is more polar than the alkyl amine and gives different properties.

2. Reaction with Ethylene Oxide or Propylene Oxide or Mixtures Thereof

2a. Reaction with Oxide (Alkyl Di-amines)

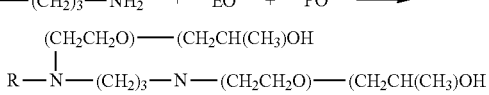

In this case ethylene oxide (EO) is reacted first with no catalyst, followed by addition of base catalyst and a mole of propylene oxide (PO).

As above in the case of reaction with acrylic acid it will be clearly noted the result is two tertiary amines. This is a necessary step for carrying out the subsequent reactions.

2a. Reaction with Oxide (Alkyl Di-amines)

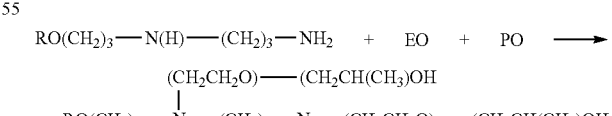

In this case ethylene oxide (EO) is reacted first with no catalyst, followed by addition of base catalyst and a mole of propylene oxide (PO).

As above in the case of reaction with acrylic acid, it will be clearly noted the result is two tertiary amines. This is a necessary step for carrying out the subsequent reactions.

The ether diamine is more polar than the alkyl amine and gives different properties.

The tertiary amines shown above are reacted with of 1,3 dichloro, 2 hydroxy propane and a mixture a mono tertiary amine in a polar solvent to give the product of the present invention.

The polymerization process includes the reaction of (a) a monofunctional tertiary amine acting as the chain terminator unit, (b) the 1,3 dichloro 2 hydroxy-propyl propane and (c) the difunctional tertiary amine. The product of the present invention is thereby attained is either a polyquaternium or a polyamphoteric. The higher the concentration of monofunctional tertiary amine, the lower the value of "x". If no di-tertiary amine is added, x is 0, resulting in a non-polymeric species. The polymer is not made with vinyl monomer, thereby making it vinyl monomer free and avoiding the toxicological problems inherent to levels of unreacted monomer left in vinyl polymers.

The compatibility of this novel quaternary compounds of the invention with human tissue, i.e., dermal and eye tissue has been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

RAW MATERIALS

Example 1

Acrylic Acid

Acrylic Acid is an item of commerce and conforms to the following structure;

$CH_2=CH-C(O)OH$

Example 2

Ethylene oxide is an item of commerce and conforms to the following structure:

Example 3

Propylene oxide is an item of commerce and conforms to the following structure:

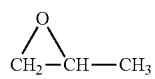

Example 4

1,3 dichloro 2 hydroxypropane an item of commerce and conforms to the following structure:

$Cl-CH_2-CH(OH)CH_2Cl$

Example Monofunctional Tertiary Amines
(Examples 5-15)

Monofunctional tertiary amines confirm to the following structure:

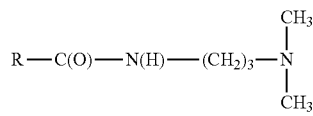

wherein;

R is alkyl having between 7 and 27 carbon atoms, and includes linear, branched, saturated, unsaturated and polyunsaturated. They are commercially available from a variety of manufacturers including Siltech LLC, Dacula, Ga.

| Example | R |
|---|---|
| 5 | $C_7H_{13}$ |
| 6 | $C_9H_{17}$ |
| 7 | $C_{11}H_{21}$ |
| 8 | $C_{13}H_{25}$ |
| 9 | $C_{15}H_{29}$ |
| 10 | $C_{17}H_{33}$ |
| 11 | $C_{19}H_{37}$ |
| 12 | $C_{21}H_{41}$ |
| 13 | $C_{23}H_{47}$ |
| 14 | $C_{25}H_{51}$ |
| 15 | $C_{27}H_{55}$ |

Diamines Examples (Examples 16-29)

The diamines of the present invention are commercially available from a variety of sources including DeGussa.

$R-N(H)-(CH_2)_3-NH_2$

| Example | R |
|---|---|
| 16 | $C_8H_{17}$ |
| 17 | $C_{10}H_{21}$ |
| 18 | $C_{12}H_{25}$ |
| 19 | $C_{14}H_{29}$ |
| 20 | $C_{16}H_{33}$ |
| 21 | $C_{18}H_{37}$ |
| 22 | $C_{20}H_{41}$ |

The ether diamines of the present invention are commercially available from a variety of sources including Tomah[3].

$R-O-(CH_2)_3-N(H)-(CH_2)_3-NH_2$

| Example | R |
|---|---|
| 23 | $C_8H_{17}$ |
| 24 | $C_{10}H_{21}$ |
| 25 | $C_{12}H_{25}$ |
| 26 | $C_{14}H_{29}$ |
| 27 | $C_{16}H_{33}$ |
| 28 | $C_{18}H_{37}$ |
| 29 | $C_{20}H_{41}$ |

Preparation of Acrylate Adducts

The reaction of the amine with acrylic acid to give di-tertiary amine is critical to the process of the present reaction, for it only the tertiary amine that can be used as specified in the reaction of the present invention.

The diamine carboxylates conform to the following structure:

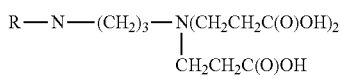

R—N—(CH$_2$)$_3$—N(CH$_2$CH$_2$C(O)OH)$_2$
|
CH$_2$CH$_2$C(O)OH

Process;

To a clean dry flask equipped with thermometer, heating and agitation is added 300 grams of acrylic acid (Example 1) and the specified number of grams of water. Heat the solution to 80° C. and add the specified number of grams of the specified amine. Addition is exothermic; slow the rate of addition to keep the water from boiling. Hold reaction at 90-95° C. for 12 hours. The products are nominally 35% solid solutions by weight and are used without purification.

| | Amine Reactant | | |
|---|---|---|---|
| Example | Example | Grams | Water (Grams) |
| 30 | 16 | 191.0 | 911.0 |
| 31 | 17 | 219.0 | 963.0 |
| 32 | 18 | 237.0 | 997.0 |
| 33 | 19 | 265.0 | 1049.0 |
| 34 | 20 | 293.0 | 1101.0 |
| 35 | 21 | 321.0 | 1524.0 |
| 36 | 22 | 349.0 | 1205.0 |

The ether diamine carboxylates conform to the following structure:

R—O—(CH$_2$)$_3$—N—(CH$_2$)$_3$—N(CH$_2$CH$_2$C(O)OH)$_2$
|
CH$_2$CH$_2$C(O)OH

Process;

To a clean dry flask equipped with thermometer, heating and agitation is added 300 grams of acrylic acid (Example 1) and enough water to make the final concentration of solids 35% by weight. Heat the solution to 80° C. and add the specified number of grams of the specified amine. Addition is exothermic; slow the rate of addition to keep the water from boiling. Hold reaction at 90-95° C. for 12 hours. The products are nominally 35% solid solutions by weight and are used without purification.

| | Amine Reactant | | |
|---|---|---|---|
| Example | Example | Grams | Water (Grams) |
| 37 | 23 | 202.0 | 932.0 |
| 38 | 24 | 230.0 | 984.0 |
| 39 | 35 | 258.0 | 1036.0 |

| | Amine Reactant | | |
|---|---|---|---|
| Example | Example | Grams | Water (Grams) |
| 40 | 36 | 286.0 | 1138.0 |
| 41 | 37 | 314.0 | 1140.0 |
| 42 | 28 | 342.0 | 1192.0 |
| 43 | 29 | 370.0 | 1244.0 |

Preparation of Alkoxylate Adducts

The reaction of the amine with ethylene oxide, propylene oxide or mixtures thereof to give di-tertiary amine is critical to the process of the present reaction, for it only the tertiary amine that can be used as specified in the reaction of the present invention.

The diamine alkoxylates conform to the following structure:

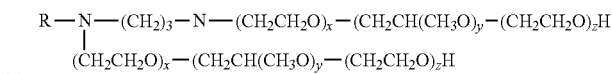

R—N—(CH$_2$)$_3$—N—(CH$_2$CH$_2$O)$_x$—(CH$_2$CH(CH$_3$)O)$_y$—(CH$_2$CH$_2$O)$_z$H
|
(CH$_2$CH$_2$O)$_x$—(CH$_2$CH(CH$_3$)O)$_y$—(CH$_2$CH$_2$O)$_z$H

Process;

To a clean dry reaction flask, add the specified number of grams of the specified diamine (Examples 16-29). Apply nitrogen Begin heating to 140-150° C. Apply vacuum once at temperature and hold for 30-40 minutes. Add the first mole of ethylene oxide or propylene oxide at 140-150° C. and 45 psig. The first mole is added to the amine without catalyst, since the amine is sufficiently reactive toward the epoxide group as not to need reaction. Once complete the reacting species is hydroxyl which is far less reactive and requires addition of catalyst. It will be quite clear that the first mole is added since reaction will cease and the consumption of alkylene oxide at constant pressure. At this point, cease addition of the ethylene oxide or propylene oxide and add 0.1% NaOCH$_3$ (sodium methylate) based upon the entire batch size (amine and total oxide to add). Resume addition of oxide. After all the specified number of grams of ethylene oxide and propylene oxide are added, hold at 140-150° C. for one hour. Then apply vacuum to remove volatile materials is any. Cool to ambient. Product is used without and additional purification.

| | Amine Reactant | | | | |
|---|---|---|---|---|---|
| Example | Example | Grams | EO 1 | PO | EO 2 |
| 44 | 16 | 191.0 | 44.0 | 0.0 | 0.0 |
| 45 | 17 | 219.0 | 440.0 | 0.0 | 0.0 |
| 46 | 18 | 237.0 | 440.0 | 59.0 | 44.0 |
| 47 | 19 | 265.0 | 220.0 | 118.0 | 220.0 |
| 48 | 20 | 293.0 | 0.0 | 590.0 | 0.0 |
| 49 | 21 | 321.0 | 0.0 | 590.0 | 220.0 |
| 50 | 22 | 349.0 | 880.0 | 1180.0 | 880.0 |

The ether diamine alkoxylates conform to the following structure:

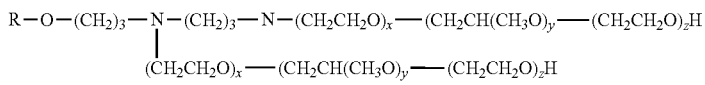

Process

To a clean dry reaction flask, add the specified number of grams of the specified diamine (Examples 16-29). Apply nitrogen Begin heating to 140-150° C. Apply vacuum once at temperature and hold for 30-40 minutes. Add the first mole of ethylene oxide or propylene oxide at 140-150° C. and 45 psig. The first mole is added to the amine without catalyst, since the amine is sufficiently reactive toward the epoxide group as not to need reaction. Once complete the reacting species is hydroxyl which is far less reactive and requires addition of catalyst. It will be quite clear that the first mole is added since reaction will cease and the consumption of alkylene oxide at constant pressure. At this point, cease addition of the ethylene oxide or propylene oxide and add 0.1% NaOCH$_3$ (sodium methylate) based upon the entire batch size (amine and total oxide to add). Resume addition of oxide. After all the specified number of grams of ethylene oxide and propylene oxide are added, hold at 140-150° C. for one hour. Then apply vacuum to remove volatile materials if any. Cool to ambient. Product is used without and additional purification.

| | Amine Reactant | | | | |
|---|---|---|---|---|---|
| Example | Example | Grams | EO 1 | PO | EO 2 |
| 51 | 23 | 202.0 | 44.0 | 0.0 | 0.0 |
| 52 | 24 | 230.0 | 0.0 | 0.0 | 220.0 |
| 53 | 35 | 258.0 | 0.0 | 590.0 | 0.0 |
| 54 | 36 | 286.0 | 880.0 | 0.0 | 880.0 |
| 55 | 37 | 314.0 | 880.0 | 1180.0 | 880.0 |
| 56 | 28 | 342.0 | 440.0 | 59.0 | 220.0 |
| 57 | 29 | 370.0 | 88.0 | 59.0 | 440.0 |

Preparation of the Compounds of the Present Invention

Into a suitable reaction flask is charged the specified number of grams of the specified solvent. Next, add the specified number of grams of 1,3 dichloro 2 hydroxy propane. Heat is applied to 90° C. Next, the specified number of grams of the specified tertiary diamine (example 30 to 57), followed by the specified number of grams of the specified mono tertiary amine (examples 5-15) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C. for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

EXAMPLE

| | Di-tertiary Amine | | Mono tertiary Amine | | Example 4 | |
|---|---|---|---|---|---|---|
| Example | Example | Grams | Example | Grams | Grams | x Value |
| 58 | 30 | 1402.9 | 5 | 450.0 | 66.0 | 1 |
| 59 | 31 | 444.8 | 6 | 50.6 | 19.8 | 3 |
| 60 | 32 | 6137.1 | 7 | 562.0 | 264.0 | 4 |
| 61 | 33 | 161.4 | 8 | 6.2 | 6.6 | 10 |
| 62 | 34 | 338.8 | 9 | 6.7 | 13.2 | 20 |
| 63 | 35 | 887.1 | 10 | 7.3 | 33.0 | 50 |
| 64 | 36 | 1854.3 | 11 | 7.8 | 660.0 | 100 |
| 65 | 37 | 14342.8 | 12 | 8.4 | 6.6 | 1000 |
| 66 | 38 | 30285.7 | 13 | 9.0 | 1320.0 | 2000 |
| 67 | 39 | 797.4 | 14 | 9.5 | 33.0 | 50 |
| 68 | 40 | 117.2 | 15 | 10.1 | 4.6 | 7 |
| 69 | 41 | 175.4 | 5 | 4.5 | 6.6 | 10 |
| 70 | 42 | 91.7 | 6 | 5.0 | 3.3 | 5 |
| 71 | 43 | 114.9 | 7 | 5.6 | 4.0 | 6 |
| 72 | 44 | 235.0 | 8 | 618.0 | 66.0 | 1 |
| 73 | 45 | 1977.0 | 9 | 674.0 | 198.0 | 3 |
| 74 | 46 | 7800.0 | 10 | 730.0 | 660.0 | 10 |
| 75 | 47 | 823.0 | 11 | 7.9 | 66.0 | 100 |
| 76 | 48 | 883.0 | 12 | 8.4 | 66.0 | 1000 |
| 77 | 49 | 22620.0 | 13 | 9.0 | 1320.0 | 2000 |
| 78 | 50 | 328.9 | 14 | 9.5 | 66.0 | 10 |
| 79 | 51 | 123.0 | 15 | 10.1 | 33.0 | 50 |
| 80 | 52 | 3150.0 | 5 | 450.0 | 462.0 | 7 |
| 81 | 53 | 1696.0 | 6 | 506.0 | 132.0 | 2 |
| 82 | 54 | 10230.0 | 7 | 562.0 | 330.0 | 5 |
| 83 | 55 | 2603.2 | 8 | 6.2 | 52.8 | 80 |
| 84 | 56 | 636.6 | 9 | 6.7 | 36.9 | 60 |
| 85 | 57 | 2392.5 | 10 | 7.3 | 165.0 | 250 |

The products of the present invention range from low viscosity (300 cps) to a solid gel. The key to viscosity is the degree of polymerization (d.p.) which is reflected in the "x" value. As the "x" value increases the molecular weight of the resultant polymer increases and the % by weight of the mono tertiary amine decreases. Viscosity can also be lowered by using a non-aqueous polar solvent like propylene glycol or butylene glycol.

APPLICATIONS EXAMPLES

The higher the molecular weight, the less likely the compound is to penetrate the skin. Since contact with skin is expected in washing the hair, even for hair use the higher molecular weight components are desired. The polymers of the present invention are not made by free radical polymerization. Consequently, they have no residual monomer content. This has become a major issue in selecting polymers for personal care.

The compounds of the present invention provide outstanding wet comb and conditioning properties to hair. They reduce static build up and provide gloss. The polymers of the present invention provide an outstanding smooth dry feel on the skin. The polymers of the present invention are non-toxic, and non-irritating.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A polymer which conforms to the following structure:

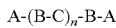

wherein:
A is

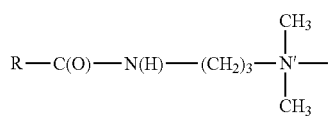

R is alkyl having between 7 and 27 carbon atoms and includes linear, branched, saturated unsaturated and polyunsaturated;
B is $CH_2-CH(OH)CH_2-$
C is:

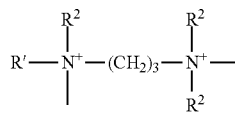

$R^1$ is selected from the group consisting of
$CH_3-(CH_2)_a-$
and
$CH_3-(CH_2)_b-O-(CH_2)_3-$
a is an integer ranging 7 and 27 carbon atoms and includes linear, branched, saturated unsaturated and polyunsaturated;
b is an integer ranging 7 and 27 carbon atoms and includes linear, branched, saturated unsaturated and polyunsaturated;
$R^2$ is selected from the group consisting of
$-(CH_2CH_2O)_x-(CH_2CH(CH_3)O)y-(CH_2CH_2O)_zH$
and
$-(CH_2)_2C(O)O^-M^+$
M is selected from the group consisting of Na, K, and H;
x, y and z are independently integers ranging from 0 to 20, with the proviso that x+y+z be greater than 1;
n is an integer ranging from 1 to 2000.

2. A polymer of claim 1 wherein $R^2$ is $-(CH_2CH_2O)_x-(CH_2CH(CH_3)O)y-(CH_2CH_2O)_zH$.

3. A polymer of claim 1 wherein $R^2$ is $-(CH_2)_2C(O)O^-M^+$.

4. A polymer of claim 1 wherein $R^1$ is $CH_3-(CH_2)_n-$.

5. A polymer of claim 1 wherein $R^1$ is $CH_3-(CH_2)_b-O-(CH_2)_3-$.

6. A polymer of claim 1 wherein R is $CH_3(CH_2)_6-$.

7. A polymer of claim 1 wherein R is $CH_3(CH_2)_{12}-$.

8. A polymer of claim 1 wherein R is $CH_3(CH_2)_{18}-$.

9. A process for conditioning hair, which comprises contacting the hair with an effective conditioning concentration of a quaternary compound, which conforms to the following structure:

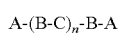

wherein:
A is

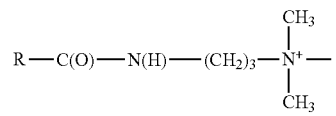

R is alkyl having between 7 and 27 carbon atoms and includes linear, branched, saturated unsaturated and polyunsaturated;
B is $CH_2-CH(OH)CH_2-$
C is:

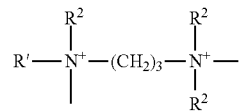

$R^1$ is selected from the group consisting of
$CH_3-(CH_2)_a-$
and
$CH_3-(CH_2)_b-O-(CH_2)_3-$
a is an integer ranging 7 and 27 carbon atoms and includes linear, branched, saturated unsaturated and polyunsaturated;
b is an integer ranging 7 and 27 carbon atoms and includes linear, branched, saturated unsaturated and polyunsaturated;
$R^2$ is selected from the group consisting of
$-(CH_2CH_2O)_x-(CH_2CH(CH_3)O)y-(CH_2CH_2O)_zH$
and
$-(CH_2)_2C(O)O^-M^+$
M is selected from the group consisting of Na, K, and H;
x, y and z are independently integers ranging from 0 to 20, with the proviso that x+y+z be greater than 1;
n is an integer ranging from 1 to 2000.

10. A process of claim 1 wherein said effective conditioning concentration ranges from 1.0% to 25% by weight.

11. A process of claim 1 wherein $R^2$ is $-(CH_2CH_2O)_x-(CH_2CH(CH_3)O)_y-(CH_2CH_2O)_zH$.

12. A process of claim 1 wherein $R^2$ is $-(CH_2)_2C(O)O^-M^+$.

13. A process of claim 1 wherein $R^1$ is $CH_3-(CH_2)_n-$.

14. A process of claim 1 wherein $R^1$ is $CH_3-(CH_2)_b-)-(CH_2)_3-$.

15. A process of claim 1 wherein R is $CH_3(CH_2)_8-$.

16. A process of claim 1 wherein R is $CH_3(CH_2)_{12}-$.

17. A process of claim 1 wherein R is $CH_3(CH_2)_{24}-$.

18. A process of claim 9 wherein R is $CH_3(CH_2)_{26}-$.

* * * * *